United States Patent [19]
Delavarenne et al.

[11] 4,152,340
[45] May 1, 1979

[54] PROCESS FOR THE PREPARATION OF ANTHRAQUINONE

[75] Inventors: Serge-Yvon Delavarenne, Francheville Le Haut; Pierre Tellier, Oullins, both of France

[73] Assignee: Produits Chimiques Ugine Kuhlmann, Paris, France

[21] Appl. No.: 826,128

[22] Filed: Aug. 19, 1977

[30] Foreign Application Priority Data

Oct. 1, 1976 [FR] France ................................ 76 29556

[51] Int. Cl.² ............................................. C07C 49/68
[52] U.S. Cl. .................................................... 260/369
[58] Field of Search .......................................... 260/369

[56] References Cited
FOREIGN PATENT DOCUMENTS
571522  3/1933  Fed. Rep. of Germany.

Primary Examiner—Allen B. Curtis
Assistant Examiner—Raymond Covington
Attorney, Agent, or Firm—Pennie & Edmonds

[57] ABSTRACT

A process which comprises reacting 1,4,4a,5,8,8a,9a,10a-octahydro-anthraquinone with nitrobenzene in the presence of a catalytic amount of a basic compound soluble in the reaction medium and of an inhibitor of free radical reactions to produce anthraquinone.

5 Claims, No Drawings

PROCESS FOR THE PREPARATION OF ANTHRAQUINONE

BACKGROUND OF THE INVENTION

It is known from the prior art that anthraquinone may be obtained on treating with air or oxygen a solution or dispersion of octahydro-anthraquinone (French Pat. No. 673,825 of Apr. 22, 1929). Another process comprises heating 1,4,4a,9a-tetrahydro-anthraquinone in the presence of nitrobenzene (British Pat. No. 895,620 of May 2, 1962). It is also possible to obtain anthraquinone by heating the 1,4,4a,5,8,8a,9a,10a-octahydro-anthraquinone in the presence of nitrobenzene, but the yield of the reaction is poor and the product obtained is not pure.

DESCRIPTION OF THE INVENTION

The applicants have found that it is possible to significantly improve the yield of anthraquinone by reacting 1,4,4a,5, 8, 8a,9a,10a-octahydro-anthraquinone with nitrobenzene in the presence of a catalytic amount of a basic compound soluble in the reaction medium and an inhibitor of free radical reactions.

The reaction can be carried out at a temperature from about 170° to 250° C., preferably from about 190° to 230° C.

The concentration of the octahydro-anthraquinone in the reaction medium may vary within large limits. For reasons of productivity, it is preferably over 10% by weight. For practical reasons related to the solubility of the products, it is generally less than 50% by weight. The preferred concentration is between about 15 and 40% by weight.

Various basic compounds can be used according to the invention as catalytic agents so long as they are soluble in the reaction medium. Some specific examples of such basic compounds include aliphatic, cycloaliphatic or aromatic amines, nitrogen heterocyclic compounds, and quaternary ammonium hydroxides. Their concentration in the medium should be at least about 0.25%. Much higher amounts could be used if desired, but there is no economic reason to do so.

The inhibitors of free radical reactions are well known and are commonly used, for example, as inhibitors of polymerization or as antioxidants. Some specific examples of such inhibitors of free radical reactions include sulphur, sulphur compounds, phenol derivatives, aryl phosphites and aromatic amines. The amount of inhibitor used should be at least about 100 ppm in the reaction medium. Again, higher amounts can, of course, be used if desired.

EXAMPLE 1

125 g of nitrobenzene, 54 g of 1,4,4a,5,8,8a,9a,10a-octahydro-anthraquinone, 2 g of piperidine and 0.2 g of sulphur are introduced into a stainless steel autoclave provided with heating and stirring devices. The mixture is heated to 200° C. and this temperature is maintained for 5 hours. The precipitate obtained is filtered off, washed with nitrobenzene, then with acetone, and dried. 44.5 g of a solid yellow product melting at 284° C. are obtained (melting point of anthraquinone, 288° C.). Chromatography shows that the product is anthraquinone of 99% purity. The yield is 84.7%.

EXAMPLE 2

Using the same reaction conditions as in Example 1, but starting from 27 g of octahydro-anthraquinone, 22.2 g of pure anthraquinone melting at 286° C. are obtained, which correspond to a yield of 85.4%.

EXAMPLES 3 to 9

Using the same reaction conditions and concentrations as in Example 1, but replacing piperidine and sulphur by other basic compounds and free radical inhibitors, results summarized in the following Table are obtained:

| Example No. | Basic Compound | Inhibitor | Weight of anthraquinone obtained | Yield |
|---|---|---|---|---|
| 3 | piperidine | trinonylphenyl phosphite | 42.3 g | 80.5% |
| 4 | piperidine | mercaptobenzothiazyl di-sulphide | 43.7 g | 83.1% |
| 5 | piperidine | methylene bis 2-2' (4-methyl-6-t.butyl-phenol) | 42.5 g | 80.8% |
| 6 | piperidine | phenyl-β-naphthylamine | 42 g | 79.9% |
| 7 | piperazine | sulphur | 43 g | 81.8% |
| 8 | trimethylbenzyl-ammonium hydroxide in 40% solution | sulphur | 41.8 g | 79.5% |
| 9 | tributylamine | sulphur | 42.8 g | 81.4% |

EXAMPLE 10

Following the same procedure as in Example 1, but heating the reaction mixture at 215° C. for 5 hours, 44.3 g of anthraquinone of 98% purity are obtained having a melting point of 283° C. The yield is 83.5%.

EXAMPLE 11

Following the same procedure as in Example 1, but heating the reaction mixture at 200° C. for 2 hours, 40.6 g of anthraquinone of 99% purity are obtained. The yield is 77.3%.

As will be apparent to those skilled in the art, the particular choice of a basic compound and of an inhibitor will vary the yield and/or purity to some degree, but all such compounds tested to date still show a significant improvement over the prior art as shown by the following examples:

EXAMPLE 12

Using the same conditions as in Example 1, but without adding sulphur, there is obtained 41.8 g of a strongly colored product which titrates 95% anthraquinone (purity). The yield is 76.4%.

EXAMPLE 13

Using the same conditions as in Example 1, but without adding piperidine, the yield of anthraquinone is 61.5%.

EXAMPLE 14

Using the same conditions as in Example 1, but without adding either the piperidine or the sulphur, the yield of anthraquinone is only 50.5%.

We claim:

1. A process for the preparation of anthraquinone which comprises reacting 1,4,4a,5,8,8a,9a,10a-octahydro-anthraquinone with nitrobenzene in the presence of both a basic compound soluble in the reaction medium selected from the group consisting of piperidine, piperazine, trimethylbenzylammonium hydroxide, tributylamine and an additional inhibitor compound for free radical reactions selected from the group consisting of sulphur, trinonylphenyl phosphite, mercaptobenzothiazyldisulphide, methylene bis 2-2' (4-methyl-6-t butylphenol) and phenyl-$\beta$-naphtsylamine.

2. A process as claimed in 1 in which the base and the inhibitor are added in catalytic amount.

3. A process as claimed in 1 in which the concentration of octahydro-anthraquinone is from 10 to 50% by weight.

4. A process as claimed in 2 in which the concentration of the soluble basic compound is at least about 0.25%.

5. A process as claimed in 2 in which the concentration of the free radical reaction inhibitor is at least about 100 ppm.

* * * * *

UNITED STATES PATENT AND TRADEMARK OFFICE
CERTIFICATE OF CORRECTION

PATENT NO. : 4,152,340
DATED : May 1, 1979
INVENTOR(S) : Serge-Yvon Delavarenne and Pierre Tellier It is certified that error appears in the above-identified patent and that said Letters Patent are hereby corrected as shown below:

The Abstract, lines 1 and 2, reads "1-0a-", should read
--10a- --

Column 4, line 8, reads "naphtsylamine", should read
--naphthylamine--

Signed and Sealed this

Sixteenth Day of October 1979

[SEAL]

Attest:

RUTH C. MASON
Attesting Officer

LUTRELLE F. PARKER
Acting Commissioner of Patents and Trademarks